United States Patent
Diet et al.

(10) Patent No.: US 7,517,844 B2
(45) Date of Patent: Apr. 14, 2009

(54) ACIDIC CLEANING COMPOSITIONS COMPRISING AN ACID MIXTURE AND TERNARY SOLVENT MIXTURE

(75) Inventors: Patrick Diet, Aubin Neufchateau (BE); Jean Massaux, Olne (BE); Isabelle Leonard, Juprelle (BE)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 12/132,683

(22) Filed: Jun. 4, 2008

(65) Prior Publication Data

US 2008/0234170 A1  Sep. 25, 2008

Related U.S. Application Data

(63) Continuation of application No. 11/536,835, filed on Sep. 29, 2006, now abandoned.

(60) Provisional application No. 60/728,071, filed on Oct. 19, 2005.

(51) Int. Cl.
*C11D 3/44* (2006.01)
*C11D 1/83* (2006.01)
*C11D 7/08* (2006.01)

(52) U.S. Cl. ............... 510/238; 510/253; 510/269; 510/362; 510/421; 510/424; 510/432; 510/477

(58) Field of Classification Search ............ 510/238, 510/253, 269, 362, 421, 424, 432, 477
See application file for complete search history.

(56) References Cited

U.S. PATENT DOCUMENTS

| | | | |
|---|---|---|---|
| 4,501,680 A * | 2/1985 | Aszman et al. | 510/238 |
| 4,587,030 A * | 5/1986 | Casey | 510/406 |
| 4,749,508 A * | 6/1988 | Cockrell et al. | 510/201 |
| 5,000,867 A * | 3/1991 | Heinhuis-Walther et al. | 510/384 |
| 5,039,441 A | 8/1991 | Thomas et al. | |
| 5,192,460 A | 3/1993 | Thomas et al. | |
| 5,294,364 A | 3/1994 | Thomas et al. | |
| 5,364,551 A * | 11/1994 | Lentsch et al. | 510/100 |
| 5,462,697 A * | 10/1995 | Yianakopoulos | 510/101 |
| 5,961,736 A | 10/1999 | Borah et al. | |
| 5,961,836 A * | 10/1999 | Egraz et al. | 210/652 |
| 6,593,279 B2 * | 7/2003 | Von Krosigk et al. | 507/267 |
| 6,645,929 B2 | 11/2003 | Leonard et al. | |
| 7,186,676 B2 * | 3/2007 | Boone et al. | 510/418 |
| 2002/0187918 A1 | 12/2002 | Urban | |
| 2005/0215448 A1 * | 9/2005 | Evers et al. | 510/238 |
| 2006/0035808 A1 * | 2/2006 | Ahmed et al. | 510/499 |

FOREIGN PATENT DOCUMENTS

| | | |
|---|---|---|
| EP | 778338 | 6/1997 |
| EP | 1721961 | 11/2006 |
| GB | 2385597 | 8/2003 |
| GB | 2392167 | 2/2004 |
| WO | 19980049260 | 11/1998 |
| WO | 1999023194 | 5/1999 |

* cited by examiner

*Primary Examiner*—Charles I Boyer
(74) *Attorney, Agent, or Firm*—Michael U. Lee

(57) ABSTRACT

A composition comprising a mixing product of:
(i) a first acid having a pKa of less than 3, in an amount by weight of 1-10%,
(ii) a second acid having a pKa of greater than 3, in an amount by weight of 1-10%,
(iii) a nonionic surfactant in an amount by weight of 1-7%; and
(iv) water;
wherein the composition has a pH of less than 2.5. The composition can be used for the removal of grease, lime scale, soap scum, and rust on hard surfaces.

24 Claims, No Drawings

ACIDIC CLEANING COMPOSITIONS COMPRISING AN ACID MIXTURE AND TERNARY SOLVENT MIXTURE

CROSS REFERENCE TO RELATED APPLICATION

This application is a continuation of U.S. Ser. No. 11/536,835, filed 29 Sep. 2006 now abandoned, which claims priority to U.S. Ser. No. 60/728,071, filed on 19 Oct. 2005, the contents of each of which is incorporated herein by reference.

BACKGROUND

Cleaning compositions for use on hard surfaces are known. Hard surfaces are those typically found in bathrooms and kitchens and include a variety of different materials such as enamel, ceramic, and the like. Such surfaces include fixtures such as bathtubs, sinks, and toilets, as well as countertops. Use of certain agents such as soap and hard water frequently form deposits and stains on these surfaces. Such deposits include grease, lime scale, soap deposits ("soap scum") and rust.

Various formulations of cleaning compositions have been produced which act to remove these deposits. For example, certain acidic compositions are well-known to remove hard water deposits such as lime scale. Others remove rust. Other formulations act as degreasers. Such formulations are generally suited for one type of deposit or stain, but do not remove all classes of deposits or stains as those described herein.

Acidic cleansers are known which have been formulated to provide activity against mineral deposits, e.g., lime scale or soap scum. Typically these cleansers—for lime scale and mineral removal properties equivalent to the invention—have a low pH and are dependant upon a certain pH range to retain the desired activity. If the pH of the solution is too low, it may cause damage to the surface to be cleaned or harm to the person applying the cleanser. If the pH is too high, the cleanser's effectiveness may be reduced or lost. Also, organic acids typically have poor activity on rust stains. Finally, most commercial acidic cleaners have poor activity on greasy stains.

It would be desirable to provide a cleaning composition that acts to remove grease, lime scale deposits, soap scum, and rust.

SUMMARY OF THE INVENTION

A composition comprising a mixing product of:
(i) a first acid having a pKa of less than 3, in an amount by weight of 1-10%,
(ii) a second acid having a pKa of greater than 3, in an amount by weight of 1-10%,
(iii) a nonionic surfactant in an amount by weight of 1-7%; and
(iv) water;
wherein the composition has a pH of less than 2.5.

DETAILED DESCRIPTION OF THE INVENTION

As used throughout, ranges are used as a shorthand for describing each and every value that is within the range. Any value within the range can be selected as the terminus of the range.

The compositions as provided herein are described and claimed with reference to their ingredients, as is usual in the art. As would be evident to one skilled in the art, the ingredients may in some instances react with one another, so that the true composition of the final formulation may not correspond exactly to the ingredients listed. Thus, it should be understood that the invention extends to the product of the combination of the listed ingredients.

Described is a composition for use on hard surfaces such as those typically found in bathrooms and kitchens, especially enamel, glass, metal, hard plastic, tile, or ceramic surfaces, such as bathtubs, sinks, and countertops. The composition can be used for the removal of grease, lime scale, soap scum and rust.

The composition is an aqueous solution comprised of at least one acid which is a stronger acid, e.g., pKa of less than 3, for example an inorganic acid such as phosphoric acid, in combination with a weaker acid, e.g., pKa of greater than 3, for example an organic acid such as lactic acid, to provide and maintain a pH in the final formulation in the range of 1-2, together with surfactants and organic solvents.

A base may be added to this acidic combination to adjust the pH if required. Using the combination of acids permits the pH of the final product to be stably maintained at effective levels, e.g., below 2.5, e.g., in a range of approximately 1-2, while retaining the desired activity against lime scale, soap scum, and rust, and further permitting the use of surfactants and solvents to provide activity against grease.

In one embodiment, the composition comprises:
(i) at least one acid, having a pKa of less than 3, e.g., 0-2.8, e.g., 2-2.5, for example phosphoric acid, e.g., in an amount by weight of 1-10%, e.g., 1-6%, for example 2-5%;
(ii) at least one acid having pKa of greater than 3, e.g., 3.2 to 5, e.g., 3.5-4, for example lactic acid, e.g., in an amount by weight of 1-10%, e.g., 1-6%, for example 2-5%;
(iii) at least one surfactant, e.g., in an amount by weight of 1-10%, e.g., 2-7%, e.g., 3-5%, selected from
 (a) nonionic surfactants for example an alkoxylated alcohol nonionic surfactant, e.g., a mixture of molecules of formula I: $CH_3(CH_2)_m$—$(O$—$CH_2$—$CH_2)_n$—$OH$ wherein m is 7-15, preferably 8-10, and n represents an average degree of ethoxylation for the mixture of 1-15, e.g., mixtures comprising compounds of formula 1 wherein n is 7-9 and compounds of formula 1 wherein n is 2-3;
 (b) ionic surfactants, e.g., an anionic surfactant, e.g., a sulfonate, e.g., alkyl sulfonate, aralkyl sulfonate, or alkaryl sulfonate, for example, sodium cumene sulfonate, and
 (c) mixtures thereof; and
(iv) water;

wherein the composition has a pH of less than 2.5, e.g., 1 to 2, e.g. 1.2 to 1.8, for example about 1.5.

The composition may further comprise an organic solvent, e.g., in an amount by weight of 1-6%, e.g., 2-5%, e.g., about 3%, e.g., a lower alkanol and/or a glycol ether or diether, for example selected from ethanol, dipropyleneglycol monobutyl ether, propylene glycol n-butyl ether, and mixtures thereof.

The composition optionally further comprises other desirable constituents. Such constituents may include perfumes or fragrances, abrasive agents, disinfectants, dyes, thickening agents (e.g., polyvinylpyrrolidone or polysaccharide), radical scavengers, bleaches, and/or chelating agents. Caustic agents, e.g., sodium hydroxide, may be included in the formulation in small amounts, e.g., up to 1% by weight, to adjust and maintain the desired pH.

In one embodiment, the composition comprises:
(i) phosphoric acid in an amount by weight of 2.5-3.5%;
(ii) lactic acid in an amount by weight of 2.5-3.5%;
(iii) surfactant in an amount by weight of 3-5% comprising
   (a) compounds of formula I: $CH_3(CH_2)_m$—(O—$CH_2$—$CH_2)_n$—OH wherein m is an integer 8 to 10, and wherein the average degree of ethoxylation, n, is 2 to 10, and
   (b) an alkaryl sulfonate, for example, sodium cumene sulfonate;
(iv) an organic solvent in an amount by weight of about 3% selected from alkanols, glycol ethers, and mixtures thereof, for example, selected from ethanol, dipropylene glycol monobutyl ether, propylene glycol n-butyl ether, and mixtures thereof; and
(v) water;

wherein the composition has a pH of 1-2.

The invention also provides methods for removing stains, e.g., stains selected from lime scale, soap scum, grease and rust stains, from a hard surface, comprising applying the composition to the hard surface, and rinsing the composition off with water.

The compositions are preferably dispensed by a spray bottle to the area to be cleaned. Optionally, the pump on the spray bottle may have a foaming mechanism so that the formulation is dispensed in the form of a foam. Accordingly, the invention further provides a non-aerosol container containing the composition and having a spray pump so that the composition can be sprayed on the surface to be cleaned, e.g., wherein the spray pump is a foam-generating pump so that the formulation can be dispensed in the form of a foam.

Acids

Examples of acids having a pKa of less than 3 which are suitable for use in the present invention include inorganic acids, e.g., muriatic acid, sulfuric acid, nitric acid, and phosphoric acid; relatively strong organic acids such as maleic acid and oxalic acid; and mixtures thereof. Phosphoric acid is preferred. Phosphoric acid is available from numerous suppliers, e.g., as an 85% syrupy solution.

Examples of acids having a pKa of greater than 3 which are suitable for use in the present invention include organic acids such as acetic acid, lactic acid, hydroxyacetic acid, citric acid, levulinic acid, tartaric acid, formic acid, glycolic acid, succinic acid, glutaric acid, and mixtures thereof. Lactic acid is preferred. The lactic acid for use in the present invention may be in the form of the D isomer, L isomer or a racemic mixture thereof. Food grade lactic acid is commonly available as an 80% solution.

For purposes of this application, pKa means the pKa in dilute aqueous solution at room temperature and pressure, e.g., at ca. 25° C., using standard, art-recognized measuring techniques. For acids such as phosphoric acid, which have more than one hydrogen capable of dissociation and so have multiple pKa values, the pKa for purposes of this application refers to the ionization equilibrium with respect to the first hydrogen dissociation step. Thus the pKa of phosphoric acid for purposes of this application would be about 2.15, while the pKa of lactic acid would be about 3.86.

Surfactants

Examples of nonionic surfactants for use with the present invention include the alkoxylated alcohol nonionic Surfactants, for example, primary aliphatic alcohol ethoxylates, secondary aliphatic alcohol ethoxylates, alkylphenol ethoxylates and ethylene-oxide-propylene oxide condensates on primary alkanols, such a PLURAFACS (BASF) and condensates of ethylene oxide with sorbitan fatty acid esters such as the TWEENS (ICI). The nonionic synthetic organic detergents generally are the condensation products of an organic aliphatic or alkyl aromatic hydrophobic compound and hydrophilic ethylene oxide groups. Practically any hydrophobic compound having a carboxy, hydroxy, amido, or amino group with a free hydrogen attached to the nitrogen can be condensed with ethylene oxide or with the polyhydration product thereof, polyethylene glycol, to form a water-soluble nonionic detergent. Further, the length of the polyethenoxy chain can be adjusted to achieve the desired balance between the hydrophobic and hydrophilic elements.

The nonionic detergent class includes the condensation products of a higher alcohol (e.g., an alkanol containing about 8 to 18 carbon atoms in a straight or branched chain configuration) condensed with about 5 to 30 moles of ethylene oxide, for example, lauryl or myristyl alcohol condensed with about 16 moles of ethylene oxide (EO), tridecanol condensed with about 6 to moles of EO, myristyl alcohol condensed with about 10 moles of EO per mole of myristyl alcohol, the condensation product of EO with a cut of coconut fatty alcohol containing a mixture of fatty alcohols with alkyl chains varying from 10 to about 14 carbon atoms in length and wherein the condensate contains either about 6 moles of EO per mole of total alcohol or about 9 moles of EO per mole of alcohol and tallow alcohol ethoxylates containing 6 EO to 11 EO per mole of alcohol.

In one embodiment, the nonionic surfactants are the Neodol ethoxylates (Shell Co.), which are higher aliphatic, primary alcohol containing about 9-15 carbon atoms, such as $C_9$-$C_{11}$ alkanol condensed with 2.5 to 10 moles of ethylene oxide (NEODOL 91-2.5 or -5 or -6 or -8), $C_{12-13}$ alkanol condensed with 6.5 moles ethylene oxide (Neodol 23-6.5), $C_{12-15}$ alkanol condensed with 12 moles ethylene oxide (Neodol 25-12), $C_{14-15}$ alkanol condensed with 13 moles ethylene oxide (Neodol 45-13), and the like. Especially preferred is a mixture of Neodol 91-8 and Neodol 91-2.5 in the range of 7:1 to 3:1 weight ratio.

In one embodiment, the nonionic system comprises the mixture of a nonionic surfactant formed from a $C_9$-$C_{11}$ alkanol condensed with 2 to 3.5 moles of ethylene oxide ($C_{9-11}$ alcohol EO 2 to 3.5:1) with a nonionic surfactant formed from a $C_9$-$C_{11}$ alkanol condensed with 7 to 9 moles of ethylene oxide ($C_9$-$C_{11}$ alcohol EO 7 to 9:1), wherein the weight ratio of the $C_9$-$C_{11}$ alcohol EO 7 to 9:1 to the $C_9$-$C_{11}$ alcohol EO 2 to 3.5:1 is from 8:1 to 1:1 from preferably 7:1 to 3:1.

Additional satisfactory water soluble alcohol ethylene oxide condensates are the condensation products of a secondary aliphatic alcohol containing 8 to 18 carbon atoms in a straight or branched chain configuration condensed with 5 to 30 moles of ethylene oxide. Examples of commercially available nonionic detergents of the foregoing type are $C_{11}$-$C_{15}$ secondary alkanol condensed with either 9 EO (TERGITOL 15-S-9) or 12 EO (TERGITOL 15-S-12) marketed by Union Carbide.

Other suitable nonionic detergents include the polyethylene oxide condensates of one mole of alkyl phenol containing about 8 to 18 carbon atoms in a straight- or branched chain alkyl group with about 5 to 30 moles of ethylene oxide. Specific examples of alkyl phenol ethoxylates include nonyl phenol condensed with about 9.5 moles of EO per mole of nonyl phenol, dinonyl phenol condensed with about 12 moles of EO per mole of phenol, dinonyl phenol condensed with about 15 moles of EO per mole of phenol and di-isoctylphenol condensed with about 15 moles of EO per mole of phenol.

Commercially available nonionic surfactants of this type include IGEPAL CO-630 (nonyl phenol ethoxylate) marketed by GAF Corporation.

Also among the satisfactory nonionic detergents are the water-soluble condensation products of a $C_8$-$C_{20}$ alkanol with a heteric mixture of ethylene oxide and propylene oxide wherein the weight ratio of ethylene oxide to propylene oxide is 2.5:1 to 4:1, preferably 2.8:1 to 3.3:1, with the total of the ethylene oxide and propylene oxide (including the terminal ethanol or propanol group) being 60-85%, preferably 70-80%, by weight. Such detergents are commercially available from BASF-Wyandotte and a particularly preferred detergent is a $C_{10}$-$C_{16}$ alkanol condensate with ethylene oxide and propylene oxide, the weight ratio of ethylene oxide to propylene oxide being 3:1 and the total alkoxy content being about 75% by weight.

Condensates of 2 to 30 moles of ethylene oxide with sorbitan mono- and tri-$C_{10}$-$C_{20}$ alkanoic acid esters having a hydrophilic-lipophilic balance (HLB) of 8 to 15 also may be employed as the nonionic detergent ingredient in the described composition. These surfactants are well known and are available from Imperial Chemical Industries under the TWEEN trade name. Suitable surfactants include polyoxyethylene (4) sorbitan monolaurate, polyoxyethylene (4) sorbitan monostearate, polyoxyethylene (20) sorbitan trioleate and polyoxyethylene (20) sorbitan tristearate.

Other suitable water-soluble nonionic detergents are marketed under the trade name PLURONICS. The compounds are formed by condensing ethylene oxide with a hydrophobic base formed by the condensation of propylene oxide with propylene glycol. The molecular weight of the hydrophobic portion of the molecule is of the order of 950 to 4000 and preferably 200 to 2,500. The addition of polyoxyethylene radicals to the hydrophobic portion tends to increase the solubility of the molecule as a whole so as to make the surfactant water-soluble. The molecular weight of the block polymers varies from 1,000 to 15,000 and the polyethylene oxide content may comprise 20% to 80% by weight. Preferably, these surfactants will be in liquid form and satisfactory surfactants are available as grades L 62 and L 64.

Ionic surfactants which can be used in the composition are preferably anionic surfactants, as well known in the art. Such surfactants are useful to enhance the stability of the formulation as well as to provide additional degreasing activity. Suitable water-soluble anionic surfactants include those surface-active or detergent compounds which contain an organic hydrophobic group containing generally 8 to 26 carbons and preferably 10 to 18 carbon atoms in their molecular stricture and at least one water-solubilizing group which is a sulfonate group, so as to form a water-soluble detergent. Usually, the hydrophobic group will include or comprise a $C_8$-$C_{22}$ alkyl, aryl or acyl group. Other suitable anionic surfactants are the olefin sulfonates, including long-chain alkene sulfonates, long-chain hydroxyalkane sulfonates or mixtures of alkene sulfonates and hydroxyalkane sulfonates. Preferred anionic surfactants include alkyl sulfonates, alkyl aryl sulfonates, and aryl alkyl sulfonates, e.g., $C_{12-16}$ paraffin sulfonate or sodium cumene sulfonate. In another embodiment, the composition includes a cationic surfactant in an amount less than 0.5% by weight of the composition. In another embodiment, the composition excludes cationic surfactants.

Solvents

Organic solvents which can be used in the composition include alcohols and ethers, for example glycols or alkoxylated glycols, alkoxylated aromatic alcohols, aromatic alcohols, linear alcohols, or other glycol ethers; e.g., $C_{1-4}$ alcohols, e.g., ethanol or isopropanol, and glycol ethers and diethers, especially $C_{1-6}$ alkyl ethers of propylene glycol or dipropylene glycol, for example dipropyleneglycol monobutyl ether, propylene glycol n-butyl ether, and mixtures thereof. In one preferred embodiment, the solvents are present in a 1:1:1 mixture of dipropylene glycol mono-butyl ether, propylene glycol n-butyl ether and ethanol.

Additional optional ingredients may be included to provide added effect or to make the product more attractive. Such ingredients include perfumes or fragrances, dyes, thickening agents, abrasive agents, disinfectants, radical scavengers, bleach, chelating agents, or mixtures thereof.

Unless otherwise stated, all percents described in the examples and elsewhere in this application are in weight percents based on the total formulation as 100%. All tests and measurements are performed at room temperature and pressure unless otherwise stated. The examples and other statements of preferred ingredients, formulations and utilities are intended to illustrate rather than to limit the invention.

EXAMPLE 1

The following example illustrates a composition of the described invention as compared to other formulations of similar compositions. Unless otherwise specified, all percentages are by weight.

|  | Conventional Lime Scale Cleaning Composition Wt. % | Conventional Multi-Purpose Degreaser Wt. % | Improved Composition (Formula A) Wt. % |
| --- | --- | --- | --- |
| Phosphoric acid | 0.17 | 0.0 | 3.0 |
| Lactic acid | 0.0 | 0.0 | 3.0 |
| Phosphonate | 0.1 | 0.0 | 0.0 |
| Salicylic acid | 0.25 | 0.0 | 0.0 |
| Caustic soda | 0.0 | 0.06 | 0.35 |
| Triethanolamine | 1.05 | 0.0 | 0.0 |
| Citric acid | 6.875 | 0.137 | 0.0 |
| C9-C11 alcohol EO 7.5-8:1 | 1.125 | 1.25 | 3.0 |
| C9-C11 alcohol EO 2.5:1 | 0.0 | 0.25 | 0.55 |
| Sodium cumene sulfonate | 0.0 | 0.0 | 0.4 |
| Triethylamine lauryl sulfate | 1.5 | 0.0 | 0.0 |
| Paraffin sulfonate | 0.0 | 0.5 | 0.0 |
| Cocoamidopropyl betaine | 0.0 | 0.45 | 0.0 |
| Dipropylene glycol mono-butyl ether | 0.0 | 2.0 | 1.0 |
| Propylene glycol n-butyl ether | 0.0 | 1.0 | 1.0 |
| Ethanol | 0.0 | 1.0 | 1.0 |
| Perfume | 0.39 | 0.25 | 0.39 |
| Preservative | 0.0 | 0.02 | 0.0 |
| Water | QS | QS | QS |
| Effectiveness: |  |  |  |
| Lime Scale | Reference | Not active | Better |
| Grease | Much worse | Reference | Slightly Worse |
| Soap Scum | Reference | Much Worse | Much better |
| Rust | Almost not active | Not active | Active |

As can be seen from this example, the compound of Formula A had excellent performance on lime scale and soap scum as compared to the reference compounds, was the only formulation with clear activity against rust, and yet retained substantial effectiveness against grease.

What is claimed is:
1. A composition comprising a mixing product of:
(i) a first acid having a pKa of less than 3, in an amount by weight of 1-10%,
(ii) a second acid having a pKa of greater than 3, in an amount by weight of 1-10%,
(iii) a nonionic surfactant in an amount by weight of 1-7% comprising compounds of formula I: $CH_3(CH_2)_m-(O-CH_2-CH_2)_n-OH$ wherein m is an integer of 8 to 10, and n represents an average degree of ethoxylation for the mixture of 1-15; and
(iv) water;
wherein the composition has a pH of less than 2.5, and wherein the composition further comprises a 1:1:1 mixture by weight of ethanol, dipropylene glycol monobutyl ether, and propylene glycol n-butyl ether.

2. The composition of claim 1, wherein the first acid is phosphoric acid.

3. The composition of claim 1, wherein the second acid is lactic acid.

4. The composition of claim 1, wherein the nonionic surfactant comprises a polyethoxylated alcohol.

5. The composition of claim 1 further comprising an anionic surfactant.

6. The composition of claim 5, wherein the anionic surfactant comprises an alkylaryl sulfonate surfactant.

7. The composition of claim 5, wherein the anionic surfactant comprises sodium cumene sulfonate.

8. The composition of claim 1 further comprising an organic solvent selected from the group consisting of alkanols, glycol ethers, glycol diethers, and mixtures thereof wherein the solvent is different from the ternary solvent mixture of claim 1.

9. The composition of claim 1, wherein the amount by weight of the first acid is 2-5%.

10. The composition of claim 1, wherein the amount by weight of the second acid is 2-5%.

11. The composition of claim 6, wherein the amount by weight of anionic surfactant is 0.1-8%.

12. The composition of claim 1, wherein if the composition further comprises a cationic surfactant, it is present in an amount of less than 0.5% by weight.

13. The composition of claim 1 further comprising sodium hydroxide.

14. The composition of claim 13, wherein the amount by weight of sodium hydroxide is up to 1%.

15. The composition of claim 1, wherein the composition comprises:
a surfactant in an amount by weight of 3-5% comprising
(a) compounds of formula I: $CH_3(CH_2)_m-(O-CH_2-CH_2)_n-OH$ wherein m is an integer of 8 to 10, and wherein the average degree of ethoxylation, n, is 2 to 10, and
(b) further comprises sodium cumene sulfonate;
wherein the composition has a pH of 1-2.

16. A non-aerosol container containing the composition of claim 1 and having a spray pump to dispense the composition.

17. The non-aerosol container of claim 16, wherein the spray pump is a foam-generating pump, so that the composition can be dispensed in the form of a foam.

18. A method of removing grease, lime scale, soap scum and rust from a hard surface comprising the step of applying the composition of claim 1 onto the hard surface, and rinsing the hard surface.

19. A method for removing soap scum, lime scale, or rust from a hard surface, the method comprising applying a cleaning composition onto the hard surface and rinsing the hard surface, wherein the cleaning composition comprises:
(i) 2-5% by weight phosphoric acid;
(ii) 1-10% by weight of an organic acid having a pKa greater than 3;
(iii) 1-7% by weight of a nonionic surfactant compounds of formula I: $CH_3(CH_2)_m-(O-CH_2-CH_2)_n-OH$ wherein m is an integer of 8 to 10, and n represents an average degree of ethoxylation for the mixture of 1-15;
(iv) water;
(v) an organic solvent selected from the group consisting of alkanols, glycol ethers, glycol diethers, and mixtures thereof wherein the solvent is different from the ternary solvent mixture set forth below; and
(vi) a 1:1:1 mixture by weight of ethanol, dipropylene glycol monobutyl ether, and propylene glycol n-butyl ether.

20. A method according to claim 19, wherein the composition comprises 2-5% by weight of the organic acid.

21. A method according to claim 19, wherein the organic acid comprises lactic acid.

22. A method according to claim 19, wherein the composition further comprises an anionic surfactant.

23. A method according to claim 22, wherein the anionic surfactant comprises cumene sulfonate.

24. A method according to claim 19, wherein the composition comprises:
(i) phosphoric acid in an amount by weight of 2.5-3.5%;
(ii) lactic acid in an amount by weight of 2.5-3.5%; and
(iii) surfactant in an amount by weight of 3-5% comprising
(a) compounds of formula I: $CH_3(CH_2)_m-(O-CH_2-CH_2)_n-OH$ wherein m is an integer of 8 to 10, and wherein the average degree of ethoxylation, n, is 2 to 10, and
(b) further comprises sodium cumene sulfonate;
wherein the composition has a pH of 1-2.

* * * * *